US011690994B1

(12) United States Patent
Banik et al.

(10) Patent No.: US 11,690,994 B1
(45) Date of Patent: Jul. 4, 2023

(54) MODULAR MEDICAL CONNECTOR

(71) Applicants: Robert Banik, Hollywood, FL (US); Peter Lehel, Boca Raton, FL (US)

(72) Inventors: Robert Banik, Hollywood, FL (US); Peter Lehel, Boca Raton, FL (US)

( * ) Notice: Subject to any disclaimer, the term of this patent is extended or adjusted under 35 U.S.C. 154(b) by 301 days.

(21) Appl. No.: 16/512,045

(22) Filed: Jul. 15, 2019

Related U.S. Application Data

(60) Provisional application No. 62/697,696, filed on Jul. 13, 2018.

(51) Int. Cl.
*A61M 39/10* (2006.01)
*A61M 5/14* (2006.01)
*A61M 39/20* (2006.01)

(52) U.S. Cl.
CPC ...... *A61M 39/1011* (2013.01); *A61M 5/1413* (2013.01); *A61M 39/20* (2013.01); *A61M 2039/1083* (2013.01); *A61M 2039/1088* (2013.01)

(58) Field of Classification Search
CPC ........... A61M 39/1011; A61M 5/1413; A61M 30/20; A61M 2039/1083; A61M 2039/1088; B65D 43/0235; B65D 45/20; F16L 37/006
See application file for complete search history.

(56) References Cited

U.S. PATENT DOCUMENTS

| 722,943 | A | 3/1903 | Chappell |
| 732,662 | A | 6/1903 | Smith |
| 1,678,991 | A | 7/1928 | Marschalek |
| 1,970,631 | A | 8/1934 | Sherman |
| 2,477,598 | A | 8/1949 | Hain |
| 2,739,590 | A | 3/1956 | Yochem |
| 2,823,674 | A | 2/1958 | Yochem |
| 2,834,346 | A | 5/1958 | Adams |
| 2,875,761 | A | 3/1959 | Helmer et al. |

(Continued)

FOREIGN PATENT DOCUMENTS

| DE | 202008018507 | 2/2015 |
| EP | 0148116 A | 7/1985 |

(Continued)

OTHER PUBLICATIONS

Arai Tsugio, Pilfering Proof Cap, Jan. 1, 1996.

*Primary Examiner* — Nathan R Price
*Assistant Examiner* — Justin L Zamory
(74) *Attorney, Agent, or Firm* — Malloy & Malloy PL; Jennie S. Malloy; Peter A. Matos

(57) ABSTRACT

A modular connector assembly for a medical container may include a plurality of covers and a plurality of adapters. Each cover is connectable to a cooperatively dimensioned medical container. Each adapter is attachable in fluid sealing engagement with each cover by an interface assembly including a first interface segment formed on each of said plurality of covers and a second interface segment formed on each of said plurality of adapters. The first and second interface segments and corresponding ones of the covers and adapters are initially separable and subsequently connected to define a fluid sealing engagement between connected ones of the cover and adapter. The structural configuration of each of the plurality of adapters is variable to define a different one of a plurality of medical connector types.

19 Claims, 15 Drawing Sheets

(56) References Cited

U.S. PATENT DOCUMENTS

| | | |
|---|---|---|
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,368,673 A | 2/1968 | Johnson |
| 3,489,268 A | 1/1970 | Meierhoefer |
| 3,574,306 A | 4/1971 | Alden |
| 3,598,120 A | 8/1971 | Mass |
| 3,610,241 A | 10/1971 | LeMarie |
| 3,674,181 A | 7/1972 | Marks et al. |
| 3,700,215 A | 10/1972 | Hardman et al. |
| 3,706,307 A | 12/1972 | Hasson |
| 3,712,749 A | 1/1973 | Roberts |
| 3,726,445 A | 4/1973 | Ostrowsky et al. |
| 3,747,751 A | 7/1973 | Miller et al. |
| 3,850,329 A | 11/1974 | Robinson |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,106,621 A | 8/1978 | Sorenson |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,735,617 A | 4/1988 | Nelson et al. |
| 4,742,910 A | 5/1988 | Staebler |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A | 6/1991 | Bolton |
| 5,049,129 A | 9/1991 | Zdeb et al. |
| 5,057,093 A | 10/1991 | Clegg et al. |
| D323,392 S | 1/1992 | Byrne |
| 5,078,696 A | 1/1992 | Nedbaluk |
| 5,085,332 A | 2/1992 | Gettig et al. |
| 5,090,564 A | 2/1992 | Chimienti |
| 5,133,454 A | 7/1992 | Hammer |
| 5,135,496 A | 8/1992 | Vetter et al. |
| 5,163,922 A | 11/1992 | McElveen, Jr. et al. |
| 5,165,560 A | 11/1992 | Enniss, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,370,226 A | 12/1994 | Gollobin et al. |
| 5,380,295 A | 1/1995 | Vacca |
| 5,402,887 A | 4/1995 | Shillington |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,474,178 A | 12/1995 | DiViesti et al. |
| 5,505,705 A | 4/1996 | Galpin et al. |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,662,233 A | 9/1997 | Reid |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Lift et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| D402,766 S | 12/1998 | Smith et al. |
| 5,842,567 A | 12/1998 | Rowe et al. |
| 5,876,381 A | 3/1999 | Pond et al. |
| 5,883,806 A | 3/1999 | Meador et al. |
| 5,884,457 A | 3/1999 | Ortiz et al. |
| 5,902,269 A | 5/1999 | Jentzen |
| 5,926,922 A | 7/1999 | Stottle |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A | 9/1999 | Nishida et al. |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,216,885 B1 | 4/2001 | Guillaume |
| 6,279,746 B1 | 4/2001 | Hussaini et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 | 3/2002 | Shapeton et al. |
| 6,375,640 B1 | 4/2002 | Teraoka |
| 6,394,983 B1 | 5/2002 | Mayoral et al. |
| 6,439,276 B1 | 8/2002 | Wood et al. |
| 6,485,460 B2 | 11/2002 | Eakins et al. |
| 6,488,666 B1 | 12/2002 | Geist |
| 6,491,665 B1 | 12/2002 | Vetter et al. |
| 6,500,155 B2 | 12/2002 | Sasso |

(56) References Cited

U.S. PATENT DOCUMENTS

| | | |
|---|---|---|
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanley et al. |
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,036,661 B2 | 5/2006 | Anthony et al. |
| 7,055,273 B2 | 6/2006 | Roshkoff |
| 7,100,771 B2 | 9/2006 | Massengale et al. |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| D581,046 S | 11/2008 | Sudo |
| D581,047 S | 11/2008 | Koshidaka |
| D581,049 S | 11/2008 | Sudo |
| 7,482,166 B2 | 1/2009 | Nollert et al. |
| D589,612 S | 3/2009 | Sudo |
| 7,497,330 B2 | 3/2009 | Anthony et al. |
| 7,503,453 B2 | 3/2009 | Cronin et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,886,908 B2 | 2/2011 | Farrar et al. |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B2 | 1/2013 | Vitello |
| 8,353,869 B2 | 1/2013 | Ranalletta et al. |
| 8,413,811 B1 | 4/2013 | Arendt |
| 8,443,999 B1 | 5/2013 | Reinders |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,082,157 B2 | 7/2015 | Gibson |
| 9,101,534 B2 | 8/2015 | Bochenko |
| D738,495 S | 9/2015 | Strong et al. |
| 9,125,976 B2 | 9/2015 | Uber, III et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 3/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh |
| D831,201 S | 10/2018 | Holtz et al. |
| D820,187 S | 11/2018 | Parker |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,315,808 B2 | 6/2019 | Taylor et al. |
| 10,376,655 B2 | 8/2019 | Pupke et al. |
| D859,125 S | 9/2019 | Weagle et al. |
| 10,478,262 B1 | 11/2019 | Niese et al. |
| 10,758,684 B1 | 9/2020 | Vitello et al. |
| 10,773,067 B2 | 9/2020 | Davis et al. |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 | 3/2021 | Hunt et al. |
| 11,040,149 B1 | 6/2021 | Banik |

(56) References Cited

U.S. PATENT DOCUMENTS

| | | |
|---|---|---|
| 11,040,154 B1 | 6/2021 | Vitello et al. |
| 11,097,071 B1 | 8/2021 | Hunt et al. |
| 11,278,681 B1 | 3/2022 | Banik et al. |
| D948,713 S | 4/2022 | Banik |
| 11,357,588 B1 | 6/2022 | Vitello et al. |
| 11,413,406 B1 | 8/2022 | Vitello et al. |
| 11,426,328 B1 | 8/2022 | Ollmann et al. |
| 11,471,610 B1 | 10/2022 | Banik et al. |
| 11,523,970 B1 | 12/2022 | Vitello et al. |
| 11,541,180 B1 | 1/2023 | Vitello et al. |
| 2001/0003150 A1 | 6/2001 | Imbert |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0046962 A1 | 4/2002 | Vallans et al. |
| 2002/0079281 A1 | 6/2002 | Hierzer et al. |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0104770 A1 | 8/2002 | Shapeton et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2003/0187403 A1 | 10/2003 | Balestracci |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0173563 A1 | 9/2004 | Kim et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0169611 A1 | 8/2006 | Prindle |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0303267 A1 | 12/2008 | Schnell et al. |
| 2008/0306443 A1 | 12/2008 | Neer |
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0166311 A1 | 7/2009 | Claessens |
| 2009/0326481 A1 | 12/2009 | Swisher et al. |
| 2010/0050351 A1 | 3/2010 | Colantonio et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0076840 A1 | 3/2014 | Graux et al. |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin |
| 2014/0353196 A1 | 12/2014 | Key |
| 2015/0013811 A1 | 1/2015 | Carrel et al. |
| 2015/0048045 A1 | 2/2015 | Miceli et al. |
| 2015/0112296 A1 | 4/2015 | Ishiwata et al. |
| 2015/0136632 A1 | 5/2015 | Moir et al. |
| 2015/0182686 A1 | 7/2015 | Okihara |
| 2015/0191633 A1 | 7/2015 | De Boer et al. |
| 2015/0246185 A1 | 9/2015 | Heinz |
| 2015/0302232 A1 | 10/2015 | Strassburger et al. |
| 2015/0305982 A1 | 10/2015 | Bochenko |
| 2015/0310771 A1 | 10/2015 | Atkinson et al. |
| 2016/0067144 A1 | 3/2016 | Chang |
| 2016/0067422 A1 | 3/2016 | Davis et al. |
| 2016/0090456 A1 | 3/2016 | Ishimaru et al. |
| 2016/0136352 A1 | 5/2016 | Smith et al. |
| 2016/0144119 A1 | 5/2016 | Limaye et al. |
| 2016/0158110 A1* | 6/2016 | Swisher ............... A61M 39/10 |
| | | 29/525 |
| 2016/0158449 A1 | 6/2016 | Limaye et al. |
| 2016/0176550 A1 | 6/2016 | Vitello et al. |
| 2016/0194121 A1 | 7/2016 | Ogawa et al. |
| 2016/0250420 A1 | 9/2016 | Maritan et al. |
| 2016/0279032 A1 | 9/2016 | Davis |
| 2016/0328586 A1 | 11/2016 | Bowden et al. |
| 2016/0361235 A1 | 12/2016 | Swisher |
| 2016/0367439 A1* | 12/2016 | Davis ................... A61J 1/2089 |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1 | 8/2017 | Glaser et al. |
| 2017/0239141 A1* | 8/2017 | Davis ..................... B65D 51/24 |
| 2017/0297781 A1 | 10/2017 | Kawamura |
| 2017/0319438 A1 | 11/2017 | Davis et al. |
| 2017/0354792 A1 | 12/2017 | Ward |
| 2018/0001540 A1 | 1/2018 | Byun |
| 2018/0014998 A1 | 1/2018 | Yuki et al. |
| 2018/0064604 A1 | 3/2018 | Drmanovic |
| 2018/0078684 A1 | 3/2018 | Peng et al. |
| 2018/0089593 A1 | 3/2018 | Patel et al. |
| 2018/0098915 A1 | 4/2018 | Rajagopal et al. |
| 2018/0147115 A1 | 5/2018 | Nishioka et al. |
| 2019/0308006 A1 | 10/2019 | Erekovcanski et al. |
| 2019/0388626 A1 | 12/2019 | Okihara |
| 2022/0008645 A1 | 1/2022 | Ukai et al. |

FOREIGN PATENT DOCUMENTS

| | | |
|---|---|---|
| GB | 486367 | 6/1938 |
| JP | 08002544 | 1/1996 |
| KR | 101159987 | 6/2012 |
| WO | WO 2008/000279 | 1/2008 |
| WO | WO 2017086607 | 5/2015 |

* cited by examiner

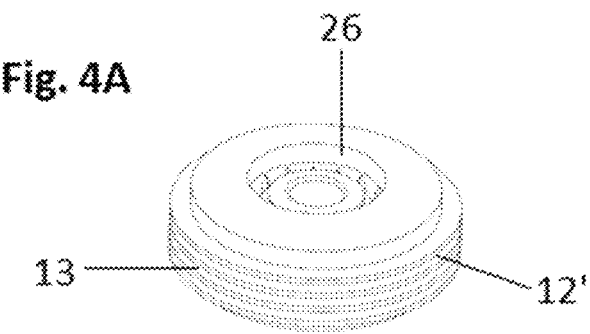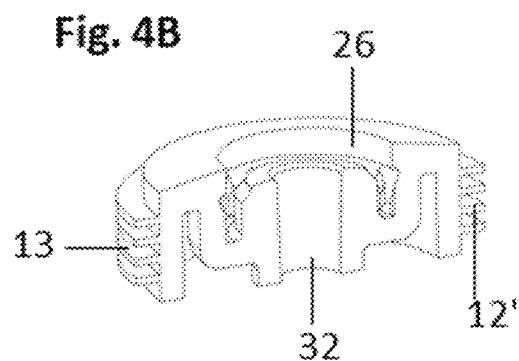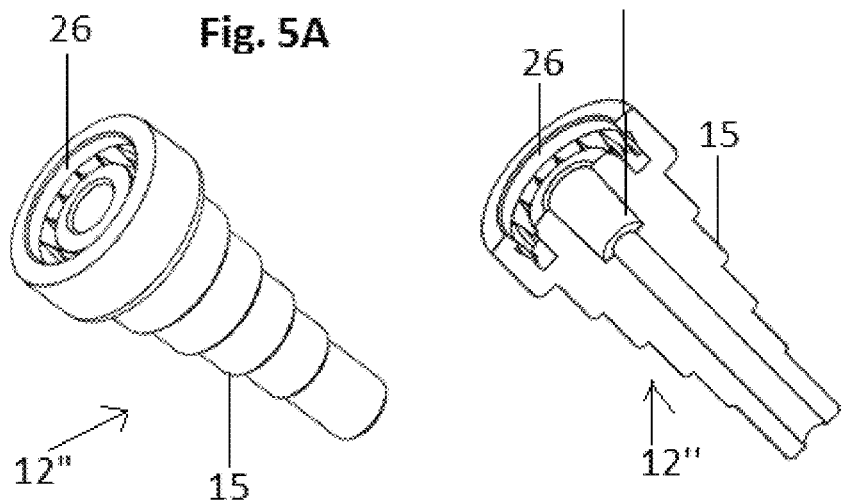

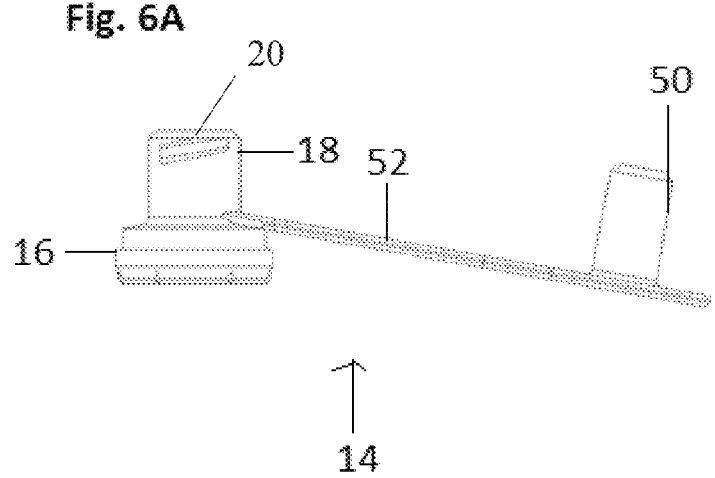

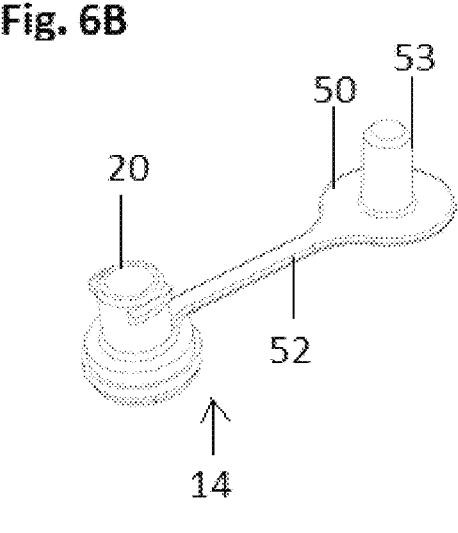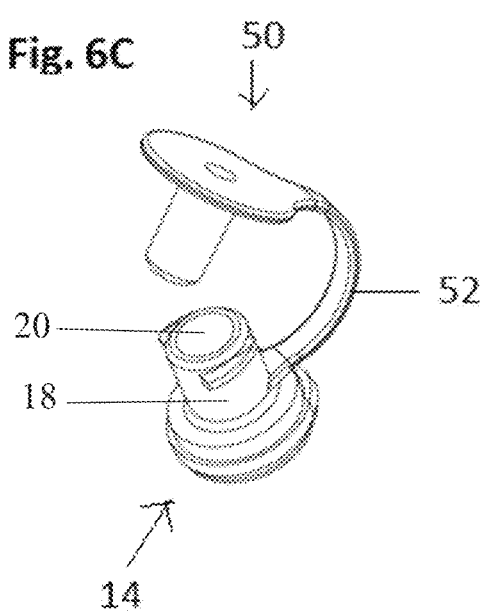

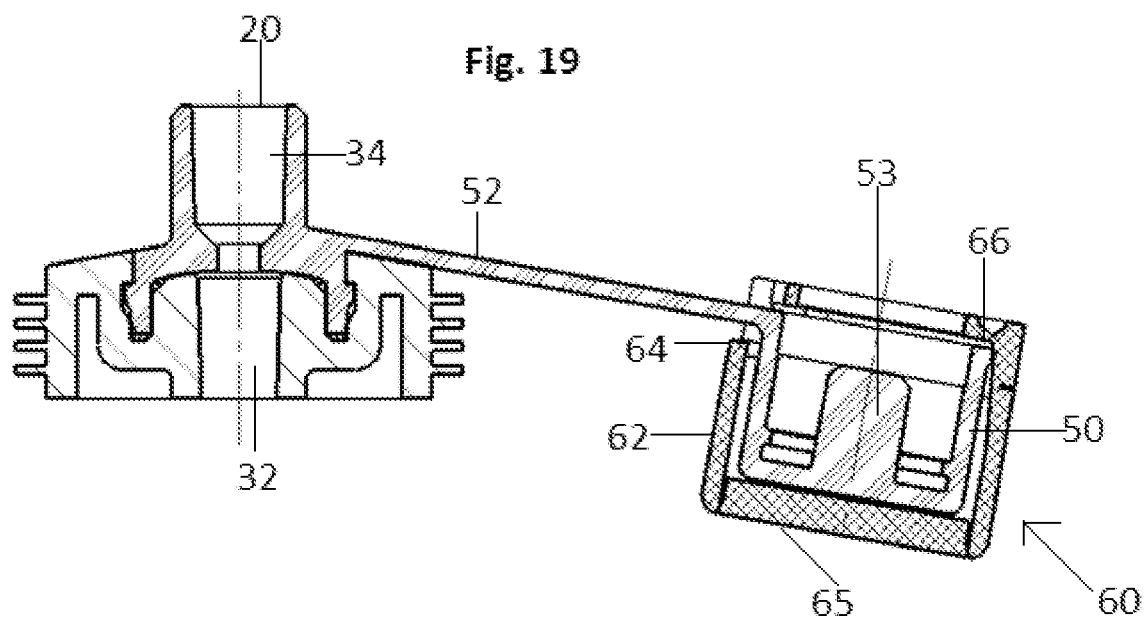

MODULAR MEDICAL CONNECTOR

CLAIM OF PRIORITY

The present application is based on and a claim of priority is made under 35 U.S.C. Section 119(e) to a provisional patent application that is currently in the U.S. Patent and Trademark Office, namely, that having Ser. No. 62/697,696 and a filing date of Jul. 13, 2018, and which is incorporated herein by reference in its entirety.

BACKGROUND OF THE INVENTION

Field of the Invention

This invention is directed to a modular connector assembly for medical containers. Each of a plurality of adapters having different structural configurations in the form of different medical connector types, may be connected to different covers. Each cover is attachable to a correspondingly dimensioned medical container.

Description of the Related Art

Medical patients, when being treated at a healthcare facility commonly receive a drug, other prescribed medication and/or other liquids in a variety of ways, but specifically including feeding tubes, intravenous tubes, catheters, etc. By way of example, a patient may be connected via a catheter, or a variety of other tubes, etc. to one or more delivery systems for purposes of receiving a prescribed medicine, or oxygen, enteral nutrition, anesthesia, etc.

The connectors operatively associated with such different delivery systems are often structurally compatible to the extent of being capable for connection to each other. However, in some cases a medicine, food composition, air, gas and/or other fluids have been accidentally delivered to a patient when a syringe or other device is wrongfully interconnected to a delivery tube. Such errors, which can cause serious injury and even death, are commonly referred to in the medical profession as "tubing misconnections".

To avoid such "tubing misconnections," there have been attempts to standardize medical connectors, based on their category of utilization, with a goal of helping to eliminate the potential for two unrelated delivery systems being attached to one another. Further by way of example, utilizing a standardized connector which is not compatible for attachment to a Luer type of connector, including slip fittings or other conventional connectors, an enteral syringe (e.g., containing a food composition intended to be taken orally), could not be connected to an IV catheter to permit entry into the blood stream intravenously, thereby avoiding potentially serious injury to patients.

The International Organization for Standardization (ISO) has taken steps to mitigate the likelihood of "tubing misconnections" through the creation of an ISO 80369 series of connectors. This has promoted patient safety by specifying international standardized designs of connectors for different healthcare application categories. Such healthcare application categories include respiratory, enteral, urology, limb cuff inflation, neuraxial and intravenous (IV). Further, the ISO has encouraged industry to be part of working groups to develop safe systems, without introducing any other safety concerns.

Part 3 of the ISO series (80369-3) is dedicated to enteral application. Accordingly, a standardized ISO enteral connector design has been developed and is known in the medical and related industries as the ISO series 80369-3 ENFit® connector. ENFit® is a registered trademark of the Global Enteral Device Supplier Association (GEDSA). The GEDSA is a nonprofit trade association formed to help introduce international standards for healthcare tubing connectors. It is comprised of manufacturers, distributors and suppliers of enteral nutrition devices worldwide and facilitates information flow, which is intended to increase patient safety and optimal delivery of enteral feeding, by reducing the risk of "tubing misconnections." Accordingly, the ENFit® connector is not compatible with a Luer type of connector or other conventional connectors, thereby eliminating or significantly reducing the possibility of a "tubing misconnection" between enteral feeding administration sets and incompatible delivery devices.

The ongoing transition to the Enteral ISO 80369-3 small bore connector standard will result in female and male threaded enteral syringes being more commonplace in the market. As indicated, this standard is intended to prevent connection between feeding tubes (enteral) and ID tubes (parenteral). However, oral dispensing is not specifically addressed. As a result, end-users of both oral syringes and enteral syringes will have a choice to stock and utilize both options or, in the alternative, standardize to the enteral syringe for oral feeding applications.

Because of the regulation of medical connections and new ISO requirements for specific connectors to prevent various drug container/delivery mis-connections, new compliant products have been and are being developed to address the demand for compliance. Previously, the standard lure slip and Luer lock design connection was used for everything from attaching a hypodermic needle and an IV interconnect to neuraxial drug preparation and enteral nutrition delivery methods. With the occurrence of human error and patient deaths due to tubing misconnections, regulation of medical connectors or fittings for specific areas of drug delivery has resulted in an increased burden of stocking and supplying dedicated devices for each connector type. Such an increase in stocking and supplying is not only costly to a hospital or other health care provider, but requires such facilities to dedicate more space for all new combination of covers, connector types and medical container sizes. The result of all these new requirements, force manufacturers to manufacture all the sizes of all the connections, including even the less frequently used sizes.

As a result, there is a need in the medical field and medical component supply industry for a modular connector assembly which facilitates the availability of covers for medical containers and that includes an adapter having a varied structural configuration. As such, the varied structural configuration of different ones of the plurality of adapters could include the integration of different connector types such as, but not limited to lure slip male and female, Luer lock male and female, oral, enteral male and female, neuraxial male and female and possibly other custom connectors.

As a result, if any such device were developed, any one of a plurality of adapters could be selectively connected to an appropriate cover, which is dimensioned to be and intended to be attached to a selected medical container. If any such device and/or adapter structure were developed, it would ideally also be operative to allow accurate administration of the contents of the medical container, while preventing tubing misconnections, of the type set forth above. In addition, the development and utilization of any such device or adapter structure would ideally optimize and reduce inventory part count by utilizing standardized connector type geometries (oral connector; male and female enteral connectors; male and female Lure slip connectors; male and female Luer lock connectors, male and female neuraxial connectors) with covers of different sizes and structures, that are appropriately dimensioned and structured to fit a given medical container. Therefore, if any such device or adapter structure were developed it should also allow manufacturers or healthcare provider to assemble appropriate covers with predetermined adapters having a correct and/or standardized connector type based on the type of administration contemplated.

SUMMARY OF THE INVENTION

The present invention is intended to present a solution to these and other needs in this field of art, and as such, is directed to a connector assembly, having a modular construction which is structured to be attached in covering and/or sealing relation to a medical container.

As used herein the term "medical container" is meant to describe various types of containers, dispensers, etc. which are structured to contain a medicinal, nutritional or other beneficial substance intended to be administered to a patient/individual. As will be described in greater detail hereinafter, the method of administration may vary and include, but not be limited to, oral, enteral, neuraxial, etc.

Accordingly, dependent at least in part on the intended method of administration, the dimensional and structural characteristics of the medical container may vary. However, the enhanced versatility of the connector assembly of the present invention, based at least partially on its modular construction, defines embodiments which may be used with a variety of different medical containers.

Therefore, the different embodiments of the connector assembly of the present invention include at least one cover, but in more practical embodiments a plurality of covers, each structured to be connected in at least partially closing relation to a correspondingly and appropriately dimensioned medical container. In more specific terms, at least some of the plurality of covers may have common structural and operative features, such as a screw-on cover or a press-in cover. As should be apparent the screw-on cover will be rotationally threaded onto the access opening of the medical container in at least partially covering relation thereto. In contrast, the press-on cover will be pushed or pressed into the interior of the access opening of the medical container. Upon insertion a frictional, sealing engagement will be established between the interior surfaces of the medical container and the exterior surfaces of the push-on cover. It is emphasized, that the plurality of adapters included in the connector assembly may be used with other types of covers such as, but not limited to a universal bottle cover.

Moreover, each of the plurality of screw-top covers and plurality of press-in covers may be available and/or utilized in different standard or customized sizes. Such different sizes are intended to correspond to the dimensional characteristics of the medical container to which they are connected. Further, depending on the method of administration, the International Organization for Standardization (ISO) has taken steps to mitigate the likelihood of "tubing misconnections" through the creation of different, standardized connector types for each method of administration.

Therefore, the modular features and characteristics of the connector assembly of the present invention comprise at least one, but in more practical embodiments, a plurality of adapters. Each of the plurality of adapters is structured to be attached in fluid sealing engagement with different ones of the predetermined plurality of covers. Further, the structural configuration of the plurality of adapters may be varied to the extent that at least one, but more practically, a number of each of the plurality of adapters are structured to define different connector types (oral, enteral, neuraxial, Lure etc.), dependent on the intended method of administration, as set forth above.

As a result, at least one embodiment of the modular connector assembly of the present invention comprises a cover dimensioned and structured to be attached to a given medical container used in combination with a selected one of the plurality of adapters. As such, the selected one of the plurality of adapters is structurally configured to have a preferred connector type integrated therein.

Additional structural features of the present invention include an interface assembly comprising a first interface segment formed on each of the plurality of covers and a second interface segment formed on each of the plurality of adapters. The first and second interface segments are initially separable due to the fact that the plurality of covers and the plurality of adapters are independently manufactured and subsequently connected. Therefore, the first and second interface segments of each of the plurality of covers and adapters are cooperatively structured to define a fluid sealing engagement therebetween and between the connected ones of the covers and adapters.

Moreover, the first and second interface segments may have a common, cooperative structure for each of the plurality of covers and adapters. The modular versatility of the connector assembly of the present invention is thereby enhanced, by allowing a selection of any one of the plurality of adapters to be connected in fluid sealing engagement with any one of the plurality of covers. A particular one of the plurality of covers will be selected to correspond to the dimensions of a particular medical container. In cooperation therewith, a particular one of the plurality of adapters, having an appropriate connector type integrated there in (oral, enteral, neuraxial, Lure etc.), will be selected for connection to the cover, based on the type of administration used to administer the contents of the medical container.

Such a common structural configuration of the interface assembly may include each of the first interface segments comprising a recess formed in an exposed portion of each of the plurality of covers. In cooperation there with, the second interface segment of each of the plurality of adapters may comprise a plug structure cooperatively configured with the aforementioned recess in the plurality of covers, to define a rotationally restrictive, plug-in connection.

When the fluid sealing engagement is established between connected first and second interface segments of corresponding closures and adapters, a flow path is established in communication between the interior of an attached medical container and an exterior thereof. The flow path may be at least partially defined by a first channel formed in the first interface segment of each of the plurality of covers and a second channel formed in the second interface segment of each of the plurality of adapters. As should be apparent, the first and second channels are disposed in fluid communication with one another so as to establish a path of fluid flow from the attached medical container to a discharge port or opening at the terminal or free end of the connected adapter.

Additional structural features of the adapter include the provision of a cap removably connected in covering, sealing relation to the discharge port or open terminal end of the connected adapter. Further, a flexible material tether may serve to permanently, but removably interconnect the cap to the remainder of the adapter so as to facilitate its sealing connection and/or removal, without loss of the cap.

In at least one embodiment, the modular connector assembly of the present invention includes a tamper evident assembly. The tamper evident assembly comprises a sleeve, having an open end, wherein the sleeve is disposed in enclosing relation to the cap. Also, a retaining member is frangibly or otherwise removably connected to the sleeve and positioned in interruptive, retaining relation to the cap, relative to the open end of the sleeve. As a result, removal of the cap from the interior of the sleeve is prevented, unless the removable retaining member is broken and separated from the sleeve. The absence of the retaining member and/or the sleeve from its enclosing relation to the cap will provide clear evidence of tampering or use.

For purposes of clarity, the structural configuration of each of the plurality of adapters may include one of an oral medical connector, an enteral medical connector, a Lure slip medical connector, a Luer lock medical connector or a neuraxial medical connector. As such, the predetermined plurality of different medical connector types which may be integrated into the plurality of adaptors include an oral connector; male and female enteral connectors; male and female Lure slip connectors; male and female Luer lock connectors, as well as male and female neuraxial connectors.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 4A is an exterior perspective view of one of a plurality of covers utilized in the connector assembly, as represented in the embodiment of FIG. 2.

FIG. 4B is a perspective interior view of the embodiment of FIG. 4A.

FIG. 5A is an exterior perspective view of one of a plurality of covers of the type represented in FIG. 3.

FIG. 5B is an interior perspective view of the embodiment of FIG. 5A.

FIG. 6A is a side view of one of a possible plurality of adapters included in the modular connector assembly of the present invention.

FIG. 6B is an isolated perspective view of the connector assembly shown in FIG. 1.

FIG. 6C is a perspective view of the embodiment of FIGS. 1 and 2.

FIG. 19 is an interior sectional view of the embodiment of FIG. 18.

Like reference numerals refer to like parts throughout the several views of the drawings.

DETAILED DESCRIPTION OF THE PREFERRED EMBODIMENT

Figure 1:
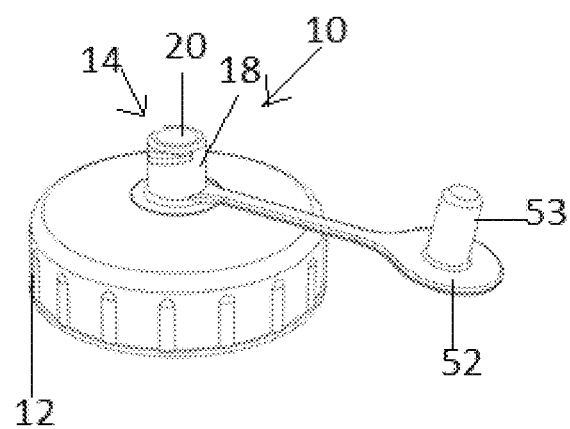
FIG. 1 is a perspective view of one embodiment of the connector assembly of the present invention, associated with or deployed on a cover.
Figure 2:
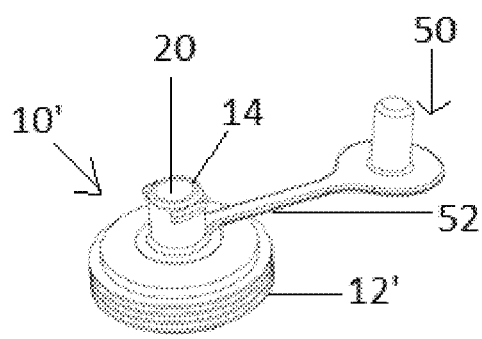
FIG. 2 is a perspective view of another embodiment of the connector assembly of the present invention.
Figure 3:
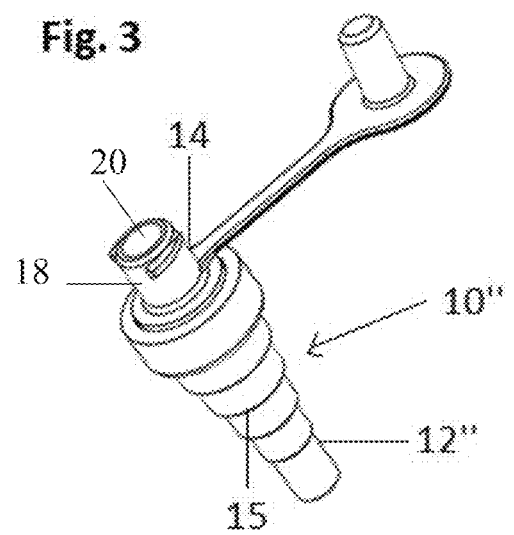
FIG. 3 is a perspective view of yet another embodiment of the connector assembly of the present invention.

As represented in the accompanying drawings and with initial reference to FIGS. 1-3, different operative embodiments of the modular connector assembly of the present invention are represented as 10, 10' and 10". Each of the represented connector assemblies includes one of a possible plurality of different covers 12, 12' and 12". Further, each of the connector assemblies 10, 10' and 10" include an adapter 14.

As represented in greater detail in FIGS. 6A-6C, each of the plurality of adapters 14 include a base 16 and a fitting section 18 having a discharge port or opening 20 at an outer end thereof. Further, each of a plurality of adapters 14 include the fitting section 18 having a varied structural configuration, which defines one of a plurality of connector type geometries.

Figure 8A:
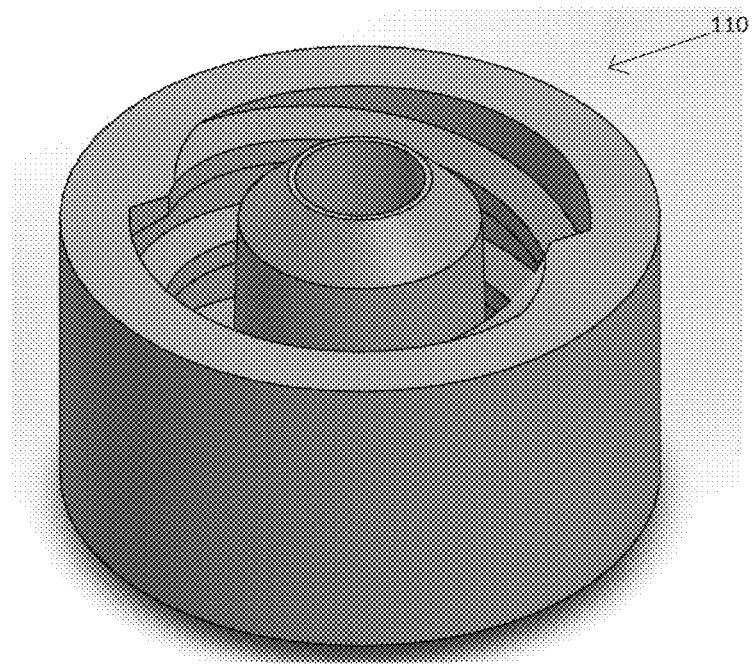
FIG. 8A is a perspective view of an enteral medical connector which may be structurally integrated into one or more of a plurality of adapters of the present invention.
Figure 8B:
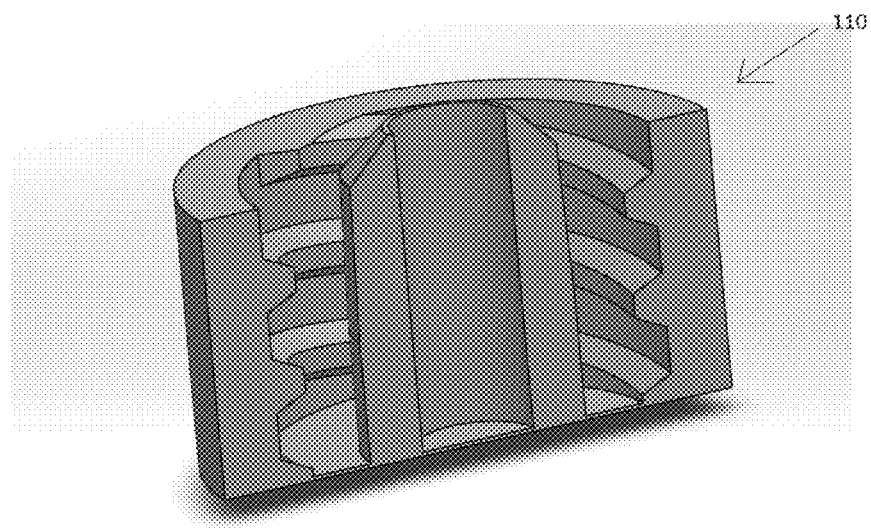
FIG. 8B is an interior perspective view of the embodiment of FIG. 8A.
Figure 9A:
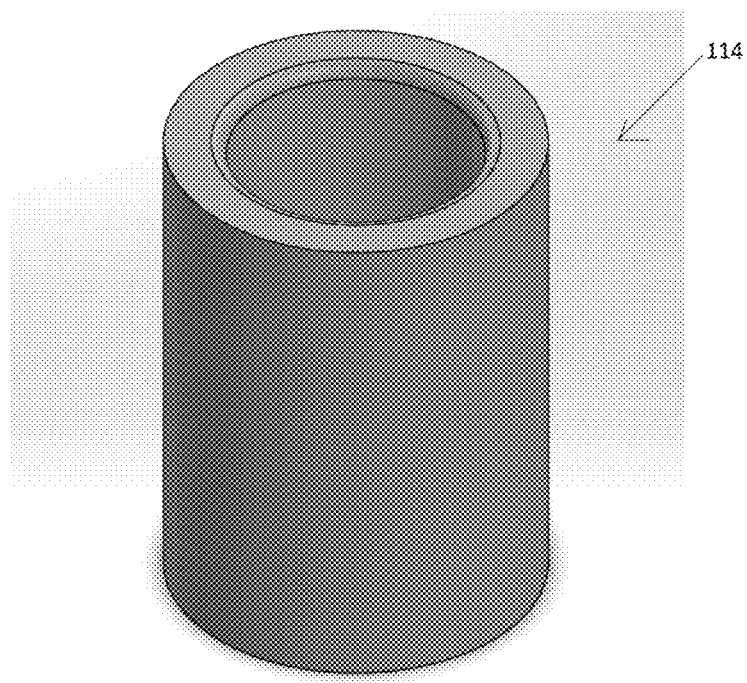
FIG. 9A is an exterior perspective view of a lure slip female medical connector type which may be structurally integrated into one or more of a plurality of adapters of the present invention.
Figure 9B:
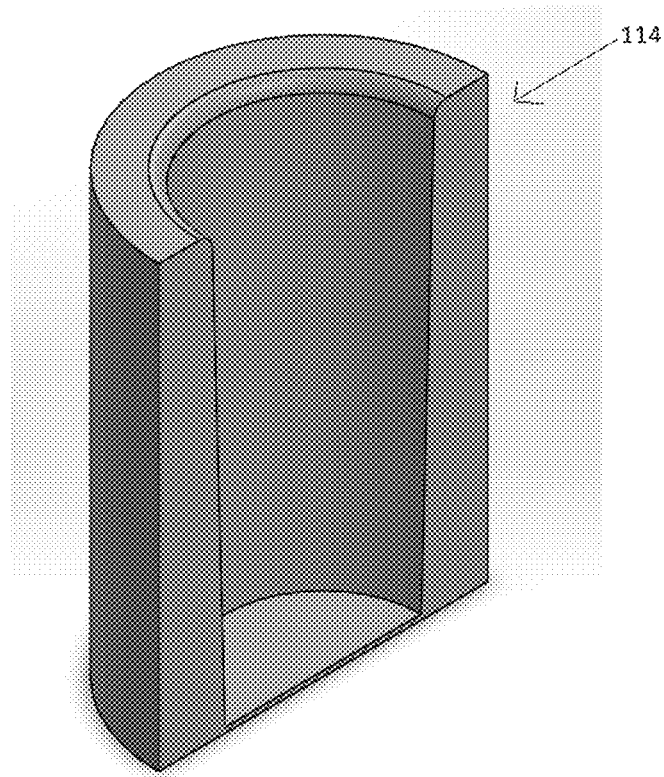
FIG. 9B is an interior perspective view of the embodiment of FIG. 9A.
Figure 10A:
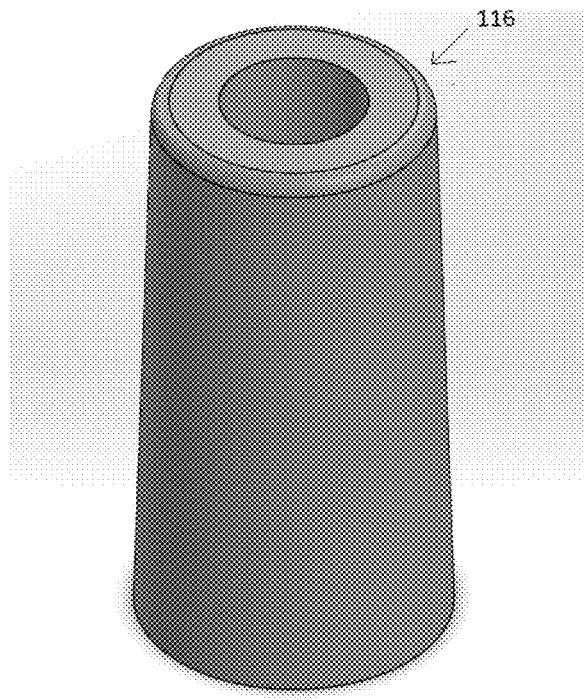
FIG. 10A is an exterior perspective view of a lure slip male medical connector type which may be structurally integrated into one or more of a plurality of adapters of the present invention.
Figure 10B:
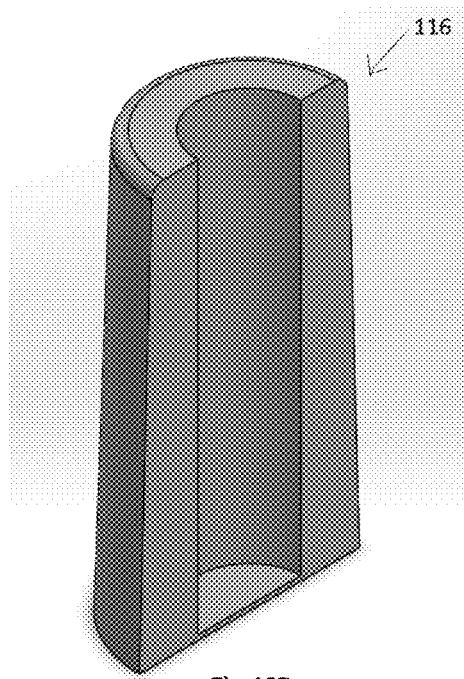
FIG. 10B is an interior perspective view of the embodiment of FIG. 10A.
Figure 11A:
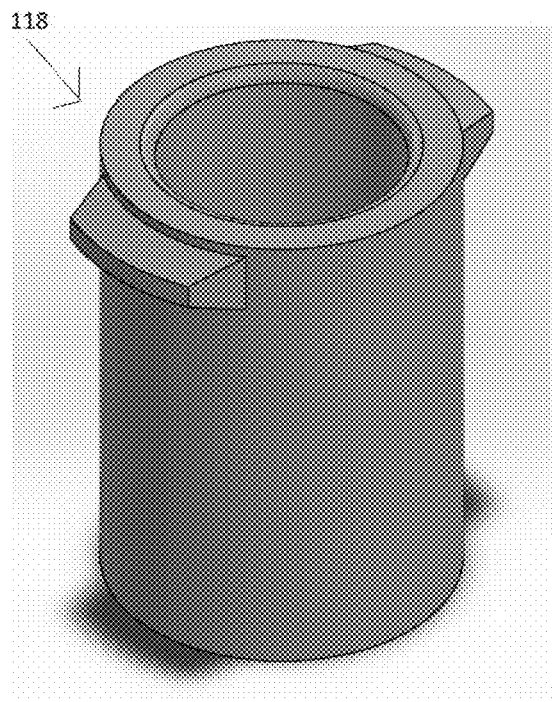
FIG. 11A an exterior perspective view of a Luer lock female medical connector type which may be structurally integrated into one or more of a plurality of adapters of the present invention.
Figure 11B:
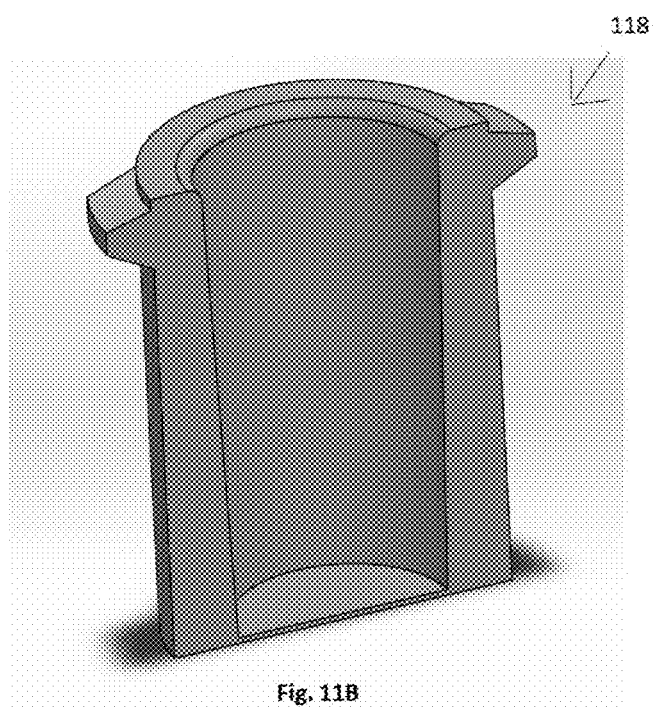
FIG. 11B is an interior perspective view of the embodiment of FIG. 11A.
Figure 12A:
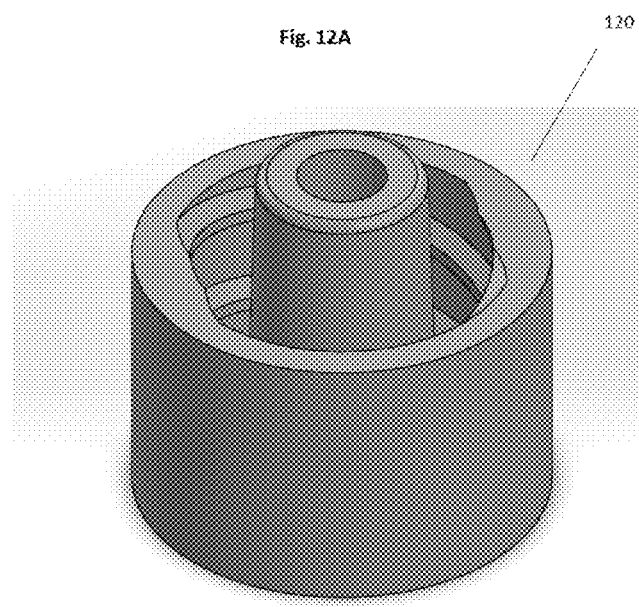
FIG. 12A is an exterior perspective view of a Luer lock male medical connector type which may be structurally integrated into one or more of a plurality of adapters of the present invention.
Figure 12B:
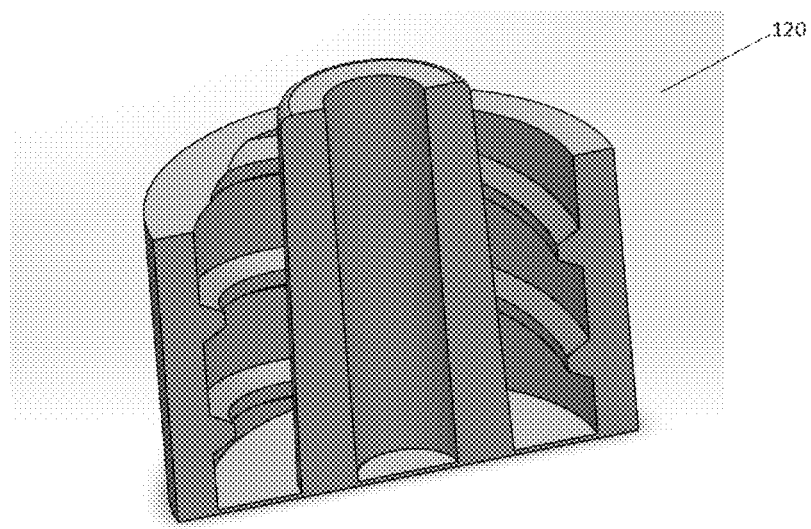
FIG. 12B is an interior perspective view of the embodiment of FIG. 12A.
Figure 13A:
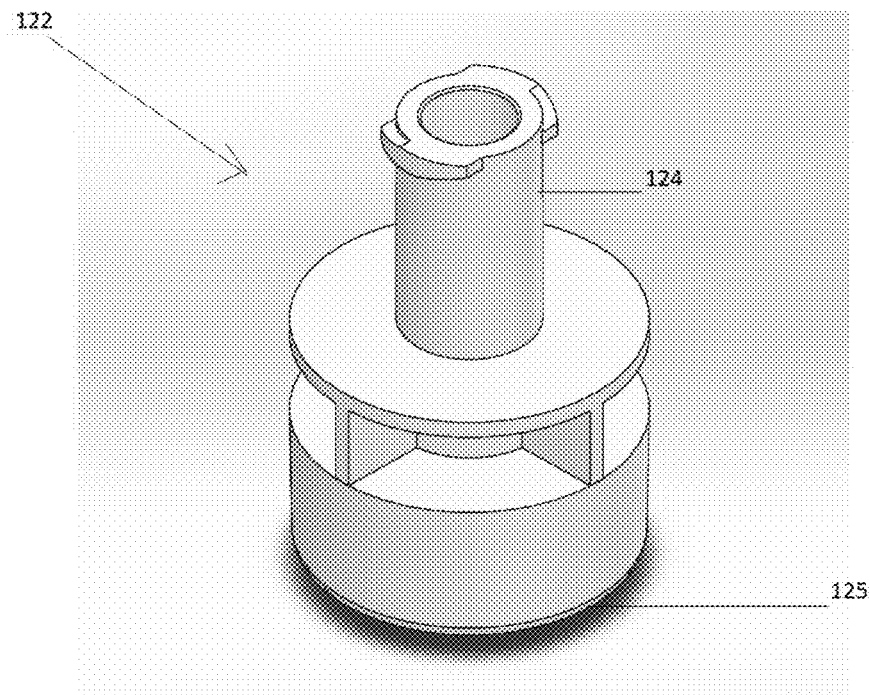
FIG. 13A is an exterior perspective view of a neuraxial female medical connector type which may be structurally integrated into one or more of a plurality of adapters of the present invention.
Figure 13B:
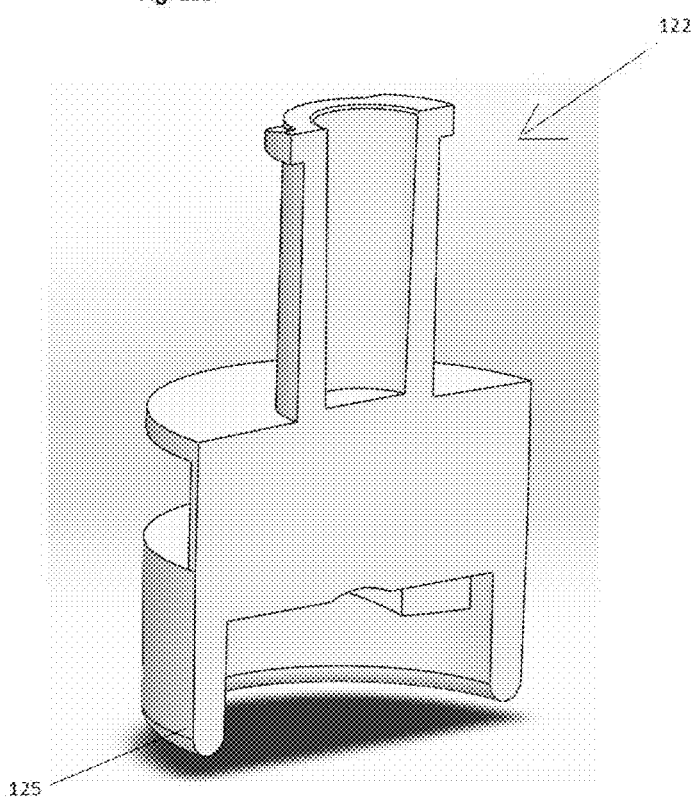
FIG. 13B is an interior perspective view of the embodiment of FIG. 13A.
Figure 14A:
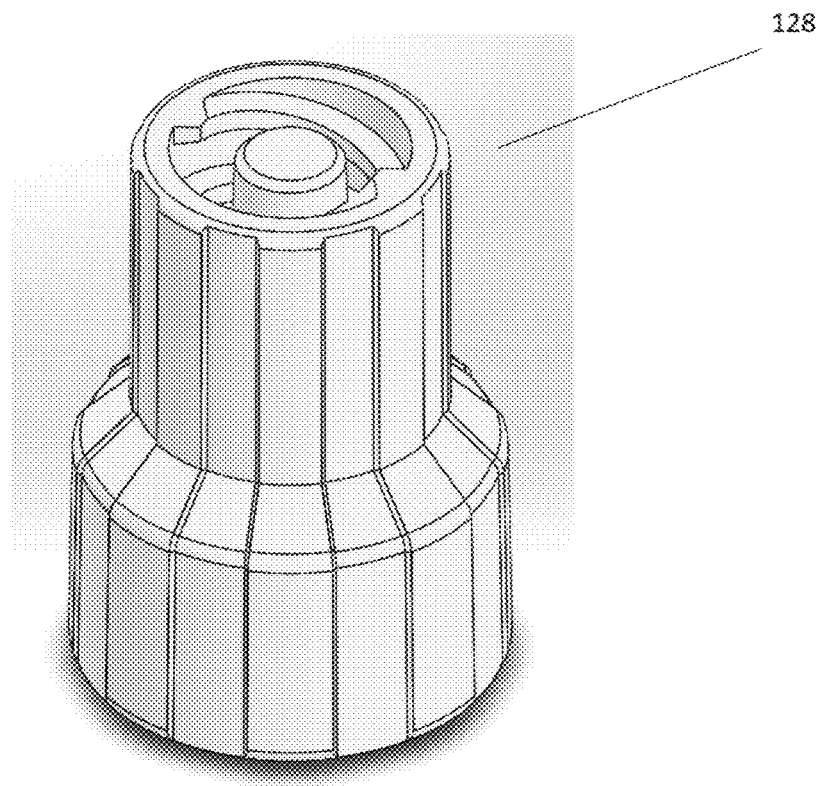
FIG. 14A is an exterior perspective view of a neuraxial male medical connector type which may be structurally integrated into one or more of a plurality of adapters of the present invention.
Figure 14B:
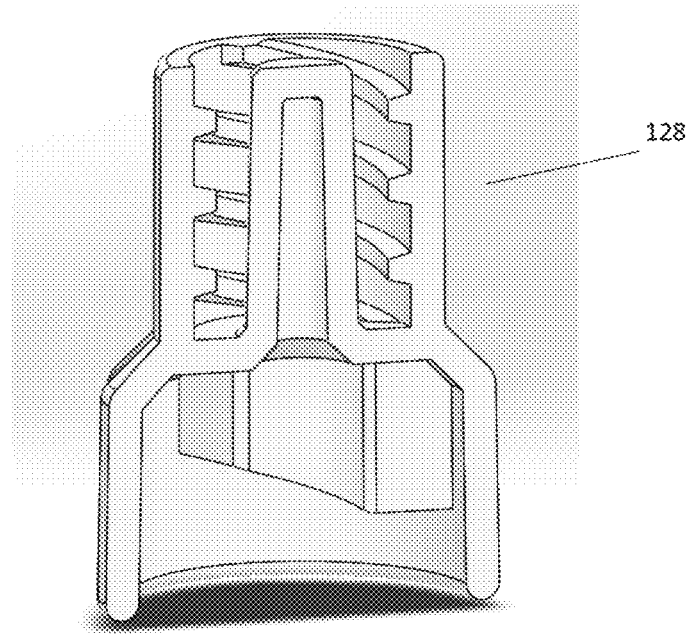
FIG. 14B is an interior perspective view of the embodiment of FIG. 14A.

Therefore, a plurality of different medical connector types may be integrated into the plurality of adapters 14, wherein the geometry of the medical connector types include an oral connector; male and female enteral connectors 110, as represented in FIGS. 8A and 8B; female Lure slip connector 114, as represented in FIGS. 9A and 9B; male lure slip connector 116 as represented in FIGS. 10A and 10B; female Luer lock connectors 118, as represented in FIGS. 11A and 11B; male Luer lock connectors 120 as represented in FIGS. 12A and 12B; neuraxial female connectors 122, as represented in FIGS. 13A and 13B and male neuraxial connectors 128, as represented in FIGS. 13A and 13B.

It is within the spirit and scope of the present invention to integrate other connector types including, but not limited to, customized medical connectors, into the fitting sections 18 of the plurality of adapters 14.

With further regard to FIGS. 8A,8B and 13A,13B, it is emphasized that the representation of the different medical connector types is provided for purposes of clarity. As such, only the "fitting portion" of the represented connector types will be integrated in the plurality of adapters 14 to define the fitting section 18 thereof. By way of nonlimiting example, and with reference to the male neuraxial connectors 122 of FIGS. 12A and 12B, the fitting portion 124 will be integrated into at least some of the plurality of adapters 14, as the fitting section 18, wherein the base portion 125 of the male neuraxial connector 122 will not be.

Additional structural features of the adapter 14 include the provision of a cap 50, removably connected in covering, sealing relation to the exposed discharge port 20 formed on the terminal end of the fitting section 18 when the adapter 14 is connected to the cover 12, 12' or 12", as represented in FIGS. 1-3. Further, a flexible material tether 52 may serve to permanently, but movably interconnect the cap 50 to the remainder of the adapter 14 so as to facilitate its sealing connection and/or removal, without loss of the cap 50.

As set forth above, each of the plurality of adapters 14 may be connected to a plurality of different covers 12, 12' and 12", wherein each of the different covers 12, 12' and 12" may be available in different standard or customized sizes. More specifically, the structural and operative features of the cover 12, in its various sizes, may define it as a screw-top cover having internal threads disposable in threaded, mating engagement with external threads adjacent the access opening of a medical connector, such as at 200, represented in FIGS. 7A and 7B.

Figures 7A, 7B:
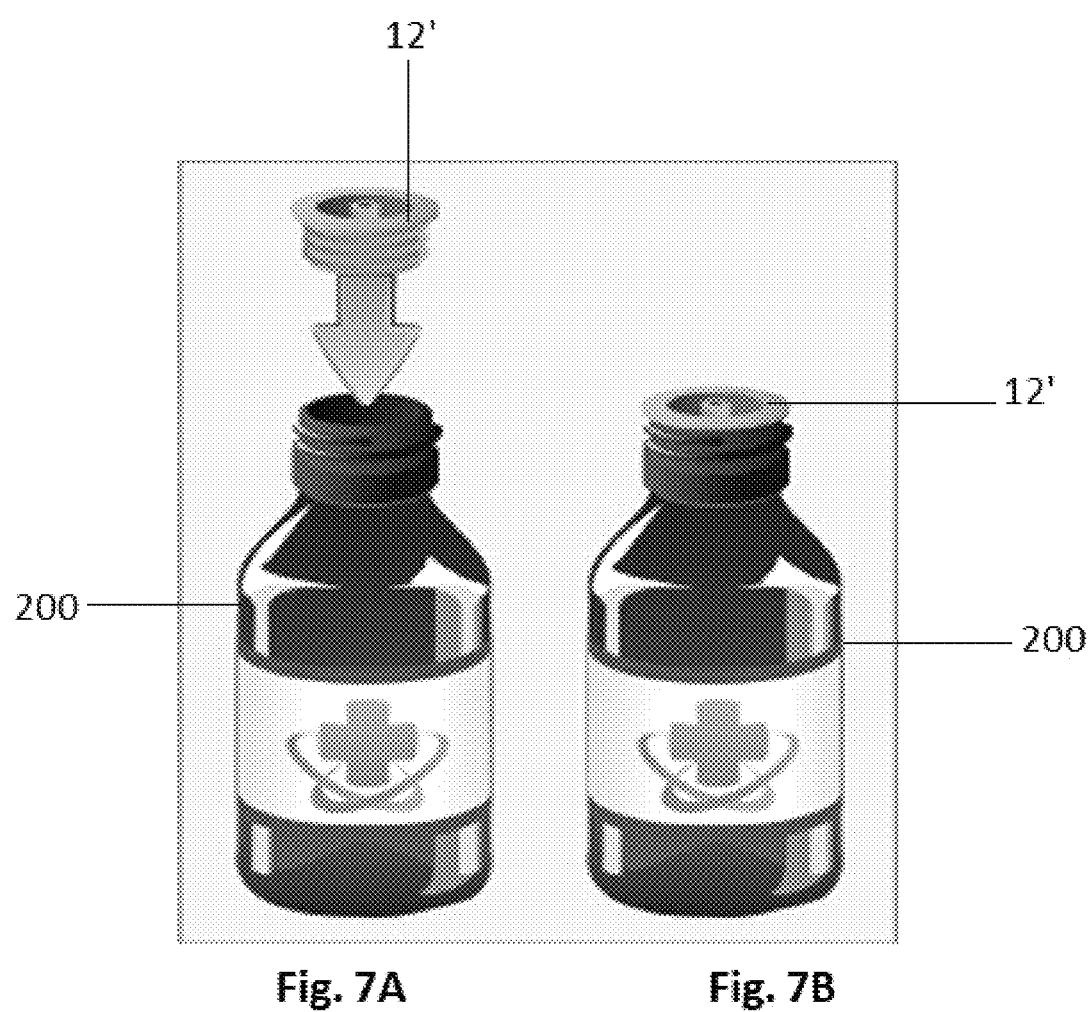
FIG. 7A illustrates one of a possible plurality of medical containers with which the modular connector assembly of the present invention may be utilized.
FIG. 7B is a perspective view of the embodiment of FIG. 7A in at least partially assembled form with one of a possible plurality of covers of the modular connector assembly of the present invention.

As represented in FIGS. 4A and 4B, cover 12' includes structural and operative features which define it as a push-in cover, wherein exterior surfaces 13 frictionally engage the interior surfaces of the medical container to form a fluid tight seal therewith, as at least partially represented in FIGS. 7A and 7B.

With reference to FIGS. 5A and 5B, cover 12" includes structural and operative features which define it as a universal bottle cover having a sealing exterior surface 15. As represented, the exterior surface 15 has successively disposed, different exterior diameters, allowing the cover 12" to be inserted into sealing engagement with different sized medical containers 200.

Figure 15:
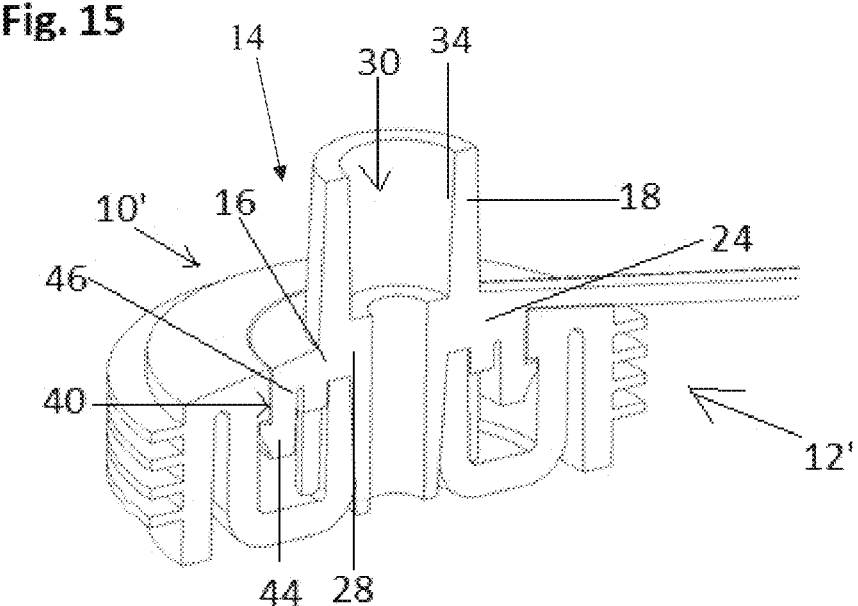
FIG. 15 is a perspective interior view of one embodiment of an assembled cover and adapter of the cover assembly of the present invention.
Figure 16:
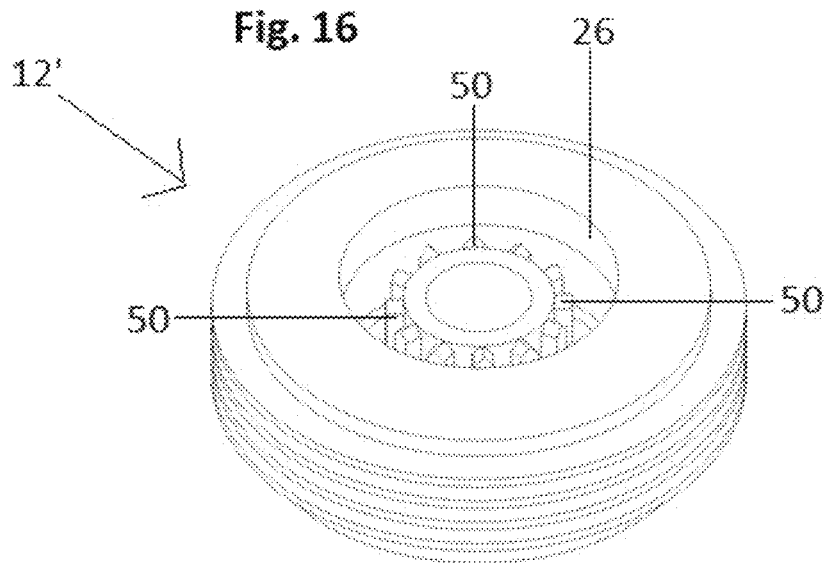
FIG. 16 is a perspective exterior view of the cover of the embodiment of FIG. 15, absent the adapter.

With reference to at least FIGS. 15 and 16, additional structural features of the present invention include an interface assembly 24. The interface assembly 24 may include a first interface segment 26 formed on the cover, and a second interface segment 28 formed on the adapter 14. By way of non-limiting example, the first interface segment 26 may comprise a recess, formed on each of the plurality of covers 12, 12' and 12" and the second interface segment 28 may comprise a plug structure, formed on or connected to the base of each of the plurality of adapters 14. The first and second interface segments 26 and 28 are initially separable due to the fact that the plurality of covers 12, 12' 12" and the plurality of adapters 14 are independently manufactured and subsequently connected into the assembled connector assembly 10, 10' and 10", as represented in FIGS. 1-3. Therefore, the first and second interface segments 26 and 28 of each of the plurality of covers 12, 12', 12" and adapters 14 are cooperatively structured to define a fluid sealing engagement therebetween and between the connected ones of the covers 12, 12', 12" and adapters 14.

Moreover, the first and second interface segments 26 and 28 may have a cooperative structure for each of the plurality of covers 12, 12', 12" and adapters 14. The modular versatility of the connector assembly 10, 10', 10" of the present invention is thereby enhanced by allowing a selection of any one of the plurality of adapters 14 to be connected in fluid sealing engagement with any one of the plurality of covers 12, 12', 12". A particular one of the plurality of covers 12, 12', 12" will be selected to correspond to the dimensions of a particular medical container 200. In cooperation therewith, a particular one of the plurality of adapters 14, having an appropriate connector type (oral, enteral, neuraxial, Lure etc.) integrated into or defining its fitting section 18, will be selected for connection to the cover 12, 12', 12", based on the type of administration used to administer the contents of the medical container 200, such as that shown in FIGS. 7A and 7B.

Such a common structural configuration of the interface assembly 24 may include each of the first interface segments comprising a recess 26 formed in an exposed face or portion of each of the plurality of covers 12, 12', 12". In cooperation therewith, the second interface segment of each of the plurality of adapters 14 may comprise a plug structure 28, cooperatively configured with the aforementioned recess 26 in the plurality of covers 12, 12', 12", to define a rotationally restrictive, plug-in connection.

When the fluid sealing engagement is established between connected first and second interface segments 26 and 28 of corresponding closures 12, 12', 12" and adapters 14, a flow path 30 is established in communication between the interior of an attached medical container, such as is shown at 200 in FIGS. 7A and 7B, and an exterior thereof. The flow path 30 may be at least partially defined by a first channel 32 formed in each of the plurality of covers 12, 12', 12" and a second channel 34 formed in the second interface segment 28 of each of the plurality of adapters 14. As should be apparent, the first and second channels 32 and 34 are disposed in fluid communication, and are most probably coaxial with one another, so as to establish a path of fluid flow from the attached medical container 200 to a discharge port 20 or opening at the terminal or free end of the connected adapter 14.

Figure 17:
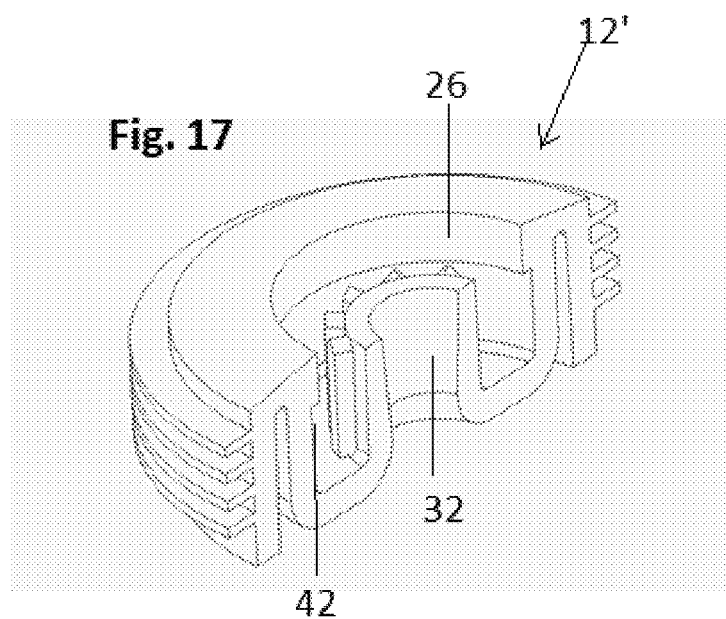
FIG. 17 is a perspective interior view of the embodiment of FIG. 16.

As represented in FIGS. 15-17, additional structural features of each of the plurality of covers 12, 12', 12" include an attachment structuring 40 which allows a plug-in connection/insertion of each of the second interface segments 28, of each of the plurality of adapters 14 into the first interface segment 26 of each of the plurality of covers 12, 12', 12". However, once a selected adapter 14 is inserted into the predetermined cover 12, 12', 12", it is prevented from being removed therefrom. As such, the attachment structuring, which is generally indicated as 40, includes an undercut portion 42 and a corresponding outwardly projecting rib 44 on the end of a skirt 46 of the second interface 28. Interlocking attachment between the undercut 42 and the projecting portion 44 of skirt 46, as represented in FIG. 15, prevent inadvertent or purposeful removal of the adapter 14 from any of the covers 12, 12', 12", unless deformation, damage, destruction, etc. is exerted on the connected adapter 14. It is of further note that while the attaching structuring 40 and other structural features associated with the interface assembly 24 and corresponding interface segments 26 and 28 are represented as being embodied into the cover 12', such structuring can also be embodied in each of the plurality of covers 12, 12', 12", etc.

As also set forth above, once a fluid sealing engagement/connection occurs between the first and second interface segments 26 and 28, a rotation resistant attachment is also established. Such rotation resistant attachment is accomplished by a plurality of ribs 50 disposed in spaced relation to one another and in substantially surrounding relation to the channel 32 of the flow path 30 associated with the first interface segment 26. The plurality of spaced ribs are disposed in frictional engagement with the interior surface portions of the aforementioned skirt 46 of the second interface segment 28, as described above.

As represented throughout the Figures, the plurality of adapters 14 may also include the aforementioned cap 50, removably connected in covering, sealing relation to the discharge port 20 or open terminal end of the connected adapter 14. Further, the flexible material tether 52 may serve to permanently, but movably interconnect the cap 50 to the remainder of the adapter 14, so as to facilitate its sealing connection and/or removal, without loss of the cap 50. The cap 50 may assume a variety of different structures. However, in the embodiments represented, the cap 50 includes a stopper 53 as shown in FIG. 19, which is disposed, dimensioned and configured to be inserted into and to seal the discharge port or opening 20 formed in each of the corresponding adapters 14.

Figure 18:
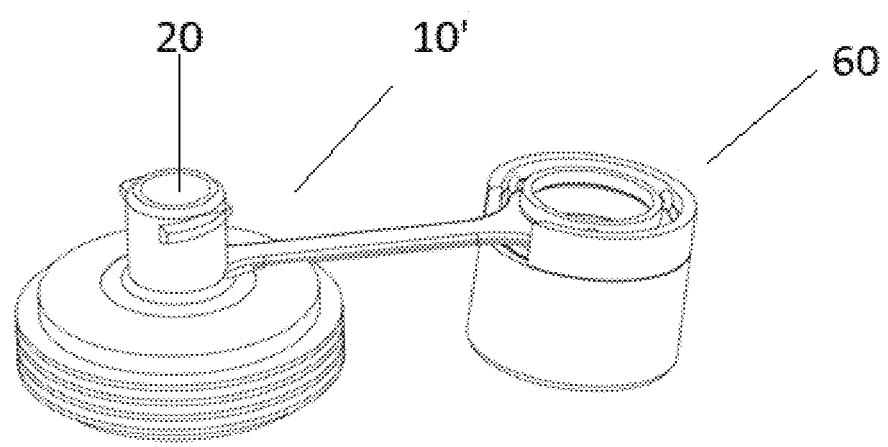
FIG. 18 is perspective view of a tamper evident assembly operatively attached to one embodiment of the cover assembly of the present invention.

As also represented in FIGS. 18-19, at least one embodiment, the modular connector assembly 10, 10', 10" of the present invention includes a tamper evident assembly, generally indicated as 60. The tamper evident assembly 60 comprises a sleeve 62, having an open end 64 and a closed end 65. When operatively positioned, the sleeve 62 is disposed in enclosing relation to the cap 50. Also, a retaining member 66 is frangibly or otherwise removably connected to the sleeve 62 and is positioned in interruptive, retaining relation to the cap 50, relative to the open end 64 of the sleeve 60. As a result, removal of the cap 50 from the interior of the sleeve 62 is prevented, unless the removable retaining member 66 is broken and separated from the sleeve 62. The absence of the retaining member 66 and/or the sleeve 62 from its enclosing relation to the cap 50 will provide clear evidence of tampering or use.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A connector assembly for a medical container having a modular construction, said connector assembly comprising:
    at least one cover structured for at least partially closing attachment to the medical container,
    an adapter connected in fluid sealing engagement to said at least one cover,
    said adapter including a base and a fitting section; said adapter further including an exposed discharge port formed on a free end of said fitting section, concurrent to said base being disposed in said fluid sealing engagement with said at least one cover,
    an interface assembly including a first interface segment formed on said cover and a second interface segment formed on said adapter,
    said first and second interface segments initially separable and cooperatively structured to define said fluid sealing engagement,
    said first and said second interface segments disposed in and cooperatively structured to define a non-removable, interlocking attachment between said interface assembly and said at least one cover, and
    said fitting section of said adapter including a variable structural configuration defining a preferred one of a predetermined plurality of different medical connector types.

2. The connector assembly as recited in claim 1 further comprising a plurality of covers, said adapter structured for operative attachment to any of said plurality of covers; at least some of said plurality of covers include a substantially common structural features and different dimensions, said different dimensions corresponding to dimensions of the medical container.

3. The connector assembly as recited in claim 1 wherein said first interface segment comprises a recess formed in an exposed portion of said at least one cover, said second interface segment comprising a plug structure cooperatively configured with said recess to define a plug-in connection.

4. The connector assembly as recited in claim 3, wherein said base is integrally attached to said fitting section, said base defining said plug structure, said plug structure cooperatively configured with said recess to define a fixed, rotationally restrictive plug-in connection therebetween.

5. The connector assembly as recited in claim 1 further comprising a flow path formed in said at least one cover and said adapter concurrent to said fluid sealing engagement therebetween; said flow path defining a path of fluid flow from an attached medical container to an exterior of said adapter, through said discharge port.

6. The connector assembly as recited in claim 5, wherein said flow path comprises a first channel formed and said at least one cover and a second channel formed in said adapter; said first and second channel disposed in fluid communication with one another and collectively defining said path of fluid flow.

7. The connector assembly as recited in claim 5 further comprising a cap removably connected to said adapter in fluid sealing relation to said discharge port.

8. The connector assembly as recited in claim 7 further comprising a tamper evident assembly including a sleeve, having an open end and disposed in enclosing relation to said cap; a retaining member removably connected to said sleeve in interruptive, retaining relation to said cap, relative to said open end.

9. The connector assembly as recited in claim 8 further comprising a tether movably interconnecting said cap and said sleeve to said adapter.

10. The connector assembly as recited in claim 1 wherein said variable structural configuration of said adapter includes one of an oral medical connector type, an enteral medical connector type, a Lure slip medical connector type, a Luer lock medical connector type or a neuraxial medical connector type.

11. A connector assembly for a medical container having a modular construction, said connector assembly comprising:
   a plurality of covers structured for at least partially closing relation to a cooperatively dimensioned medical container,
   a plurality of adapters each structured to be operatively connected in fluid sealing engagement with each of said plurality of covers,
   each of said plurality of adapters including a base and a fitting section;
   each of said plurality of adapters further including an exposed discharge port formed on a free end of said fitting section, concurrent to said base disposed in said fluid sealing engagement with a corresponding one of said plurality of covers,
   an interface assembly comprising a first interface segment formed on each of said plurality of covers and a second interface segment formed on each of said plurality of adapters,
   said first and second interface segments initially separable and disposed in and cooperatively structured to define said fluid sealing engagement,
   said first and said second interface segments disposed in and cooperatively structured to define a non-removable, interlocking attachment between said interface assembly and any one of said plurality of covers, and
   each of said fitting sections including a structural configuration defining a preferred one of a plurality of different medical connector types.

12. The connector assembly as recited in claim 11 wherein at least a first number of said plurality of covers have a substantially common structural feature and different dimensions, said different dimensions corresponding to dimensions of a connected medical container.

13. The connector assembly as recited in claim 11 wherein said first interface segment comprises a recess formed in an exposed portion of each of said plurality of covers; said second interface segment comprising a plug structure cooperatively configured with said recess to define a rotationally restrictive, plug-in connection.

14. The connector assembly as recited in claim 11 wherein fluid sealing engagement ones of said plurality of closures and said plurality of adapters collectively defining a flow path disposed in communication between an attached medical container and an exterior thereof.

15. The connector assembly as recited in claim 11 wherein said structural configuration of each of said fitting sections include one of an oral medical connector type, an enteral medical connector type, a lure slip medical connector type, a Luer lock medical connector type or a neuraxial medical connector type.

16. The connector assembly as recited in claim 11 wherein said predetermined plurality of different medical connector types include an oral connector, an enteral connector, a lure slip connector, a Luer lock connector or a neuraxial connector.

17. The connector assembly as recited in claim 11 wherein each of said plurality of adapters comprise a cap removably connected in closing, sealing relation to said discharge port.

18. The connector assembly as recited in claim 17 further comprising a tamper evident assembly including a sleeve, having an open end, said sleeve disposed in enclosing relation to said cap; a retaining member removably connected to said sleeve in interruptive, retaining relation to said cap, relative to said open end.

19. The connector assembly as recited in claim 11 wherein said first interface segment comprises a recess formed in an exposed portion of said plurality of covers; said second interface segment comprising a plug structure formed on said base; said base cooperatively configured with said recess to define said fluid sealing engagement.

* * * * *